(12) United States Patent
Allen et al.

(10) Patent No.: US 6,570,064 B1
(45) Date of Patent: May 27, 2003

(54) PLANT FLAVANONE-3-HYDROXYLASE

(75) Inventors: Stephen M. Allen, Wilmington, DE (US); Gary M. Fader, Landenberg, PA (US); Anthony J. Kinney, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 29 days.

(21) Appl. No.: 09/645,168

(22) Filed: Aug. 24, 2000

Related U.S. Application Data

(60) Provisional application No. 60/075,919, filed on Feb. 25, 1998.

(51) Int. Cl.$^7$ .......................... A01H 3/00; C07H 21/04; C07K 14/415; C12N 5/14; C12N 9/00
(52) U.S. Cl. .................. 800/278; 435/183; 435/69.1; 435/410; 435/419; 435/252.3; 435/320.1; 530/350; 530/370; 536/23.6; 536/24.1; 536/24.33; 800/295
(58) Field of Search ................. 435/183, 69.1, 435/410, 419, 252.3, 320.1; 530/350, 370; 536/23.6, 24.1, 24.33; 800/278, 295

(56) References Cited

PUBLICATIONS

Lothar Britsch Et Al., Eur. J. Biochem., vol. 217:745–754, 1993, Molecular Characterization of Flavanone 3 beta–Hydroxylases.
Richard Lukacin Et Al., Eur. J. Biochem., vol. 249:748–757, 1997, Identification of Strictly Conserved Histidine and Arginine Residues as Part of the Active Site in Petunia Hybrida Flavanone 3 beta–Hydroxylase.
National Center for Biotechnology Information General Identifier No. 729506, Accession No. Q05965, Jul. 15, 1999, Britsch, L. Et Al., Molecular Characterization of Flavanone 3 beta–hydroxylases.
National Center for Biotechnology Information General Identifier No. 550390, Accession No. X81812, Jan. 28, 1997, Charrier, B. Et Al., The Expression Pattern of Alfalfa Flavanone 3–Hydroxylase Promoter–Gus Fusion in *Nicotiana Benthamiana* Correlates with the Presence of Flavonoids Detected in Situ.
Benedicte Charrier Et Al., Plant Mol. Biol. vol. 30:1153–1168, 1996, The Expression Pattern of Alfalfa Flavanone 3–Hydroxylase Promoter–Gus Fusion in *Nicotiana Benthamiana* Correlates with the Presence of Flavonoids Detected in Situ.
National Center for Biotechnology Information General Identifier No. 729505, Accession No. Q06942, May 30, 2000, Davies, K.M., A cDNA Clone for Flavanone 3–hydroxylase from Malus.
Kevin M. Davies, Plant Phys., vol. 103:291, 1993, A cDNA Clone for Flavanone 3–hydroxylase from Malus.
National Center for Biotechnology Information General Identifier No. 3790548, Accession No. AAC68584, Oct. 26, 1998, Wisman, E. Et Al., Knock–out Mutants from an En–1 Mutagenized *Arabidopsis Thaliana* Population Generate Phenylpropanoid Biosynthesis Phenotypes.
Ellen Wisman Et Al., PNAS, vol. 95:12432–12437, 10/98, Knock–out Mutants from an En–1 Mutagenized *Abrabidopsis Thaliana* Population Generate Phenylpropanoid Biosynthesis Phenotypes.
EMBL Library Sequence Data Accession No.: X69664, Dec. 23, 1992, Davies, K.M., A cDNA clone for flavanone 3–hydroxylase from Malus.
Lothar Britsch Et Al., Eur. J. Biochem., vol. 156:569–577, 1986, Purification and characterization of (2S)–flavanone 3–hydroxylase from *Petunia hybrida*.

*Primary Examiner*—Phuong T. Bui

(57) ABSTRACT

This invention relates to an isolated nucleic acid fragment encoding a flavanone-3-hydroxylase. The invention also relates to the construction of a chimeric gene encoding all or a portion of the flavanone-3-hydroxylase, in sense or antisense orientation, wherein expression of the chimeric gene results in production of altered levels of the flavanone-3-hydroxylase in a transformed host cell.

14 Claims, 1 Drawing Sheet

Figure 1

```
SEQ ID NO:2    TLTYLAQEKTLESSFVRDEEERPKVAYNEFSDEIPVISLAGIDEVDGRRREICEKIVEACEN    68
               TLT  LA E  L S FVRDE+ERPKVAYNEFSDEIPVISLAGID+VDG+R EIC +IVEACEN
SEQ ID NO:3    TLTELAGESKLNSKFVRDEDERPKVAYNEFSDEIPVISLAGIDDVDGKRGEICREIVEACEN    63

SEQ ID NO:2    WGIFQVVDHGVDQQLVAEMTRLAKEFFALPPDEKLRFDMSGAKKGGFIVSSHLQGESVQDWR   130
               WGIFQVVDHGVD  LVA+MTRLA++FFALPP+EKLRFDMSG KKGGFIVSSHLQGE+VQDWR
SEQ ID NO:3    WGIFQVVDHGVDTSLVADMTRLARDFFALPPEEKLRFDMSGGKKGGFIVSSHLQGEAVQDWR   127

SEQ ID NO:2    EIVTYFSYPKRERDYSRWPDTPEGWRSVTEEYSDKVMGLACKLMEVLSEAMGLEKEGLSKAC   192
               EIVTYFSYP R RDYSRWPD P+GW   VTEEYS+K+MGLACKL+EVLSEAMGLEKE L+ AC
SEQ ID NO:3    EIVTYFSYPVRNRDYSRWPDKPQGWAKVTEEYSEKLMGLACKLLFVLSEAMGLEKESLTNAC   189

SEQ ID NO:2    VDMDQKVVVNYYPKCPQPDLTLGLKRHTDPGTITLLLQDQVGGLQATRDNGKTWITVQPVEA   254
               VDMDQK+VVNYYPKCPQPDLTLGLKRHTDPGTITLLLQDQVGGLQATRD+G TWITVQPVE
SEQ ID NO:3    VDMDQKIVVNYYPKCPQPDLTLGLKRHTDPGTITLLLQDQVGGLQATRDDGNTWITVQPVEG   251

SEQ ID NO:2    AFVVNLGDHAHYLSNGRFKNADHQAVVNSNHSRLSIATFQNPAPNATVYPLKIREGEKPVME   316
               AFVVNLGDH H+LSNGRFKNADHQAVVNSN  SRLSIATFQNPAP ATVYPLK+REGEK +ME
SEQ ID NO:3    AFVVNLGDHGHFLSNGRFKNADHQAVVNSNSSRLSIATFQNPAPEATVYPLKVREGEKAIME   313

SEQ ID NO:2    EPITFAEMYRRKMSKDIEIARMKKLAKEKHLQDLENEKHLQELDQKAKLEAKPLKEILA     375
               EPITFAEMY+RKM  +D+E+AR+KKLAKE+H           K  AKPL +ILA
SEQ ID NO:3    EPITFAEMYKRKMGRDLELARLKKLAKEEH------------NHKEAAKPLDQILA        357
```

US 6,570,064 B1

PLANT FLAVANONE-3-HYDROXYLASE

This application claims priority benefit of the International Application No. PCT/US99/03200 filed Feb. 16, 1999, now pending, which claim priority benefit of U.S. Provisional Application No. 60/075,919 filed Feb. 25, 1998.

FIELD OF THE INVENTION

This invention is in the field of plant molecular biology. More specifically, this invention pertains to nucleic acid fragments encoding flavanone-3-hydroxylase in plants and seeds.

BACKGROUND OF THE INVENTION

Flavonoids are plant phenolic compounds involved in leguminous plant-microbe interactions. Flavanone-3-hydroxylase, also known as Naringenin, 2-Oxoglutarate 3-Dioxygenase (EC 1.14.11.9), is an enzyme dependent on $Fe^{+2}$, molecular oxygen, 2-oxoglutarate, and ascorbate, the typical cofactors of the class 2-oxoglutarate-dependent dioxygenases. Flavanone-3-hydroxylase catalyses the 3-beta-hydroxylation of 2S-flavanones to 2R,3R-dihydroflavonols which are intermediates in the biosynthesis of flavonols, anthocyanidins, catechins and proanthocyanidins in plants.

Few of the genes encoding enzymes that regulate these pathways in plants, especially soybeans and *Impatiens balsamina*, have been isolated and sequenced. cDNAs encoding flavanone-3-hydroxylase have been isolated from petunia, *M. incana*, carnation, china aster and barley. Residues conserved among similar enzymes have been determined by sequence analysis of various related non-heme iron enzymes. Fourteen amino acids are strictly conserved of which three His and one Asp residues (positions 78, 220, 278 and 222 of the petunia flavanone-3-hydroxylase) have been determined to belong to the putative iron-binding site and an Arg (288) to be part of the 2-oxoglutarate binding site (Britsch L et al. (1993) *Eur J Biochem* 217:745–754; Lukacin R and Britsch L (1997) *Eur J Biochem* 249:748–757).

No soybean or *Impatiens balsamina* genes have yet been reported for flavanone-3-hydroxylase. Accordingly, the availability of nucleic acid sequences encoding all or a portion of flavanone-3-hydroxylase would facilitate studies to better understand the cellular control of the flavonol, anthocyanidin, catechin and proanthocyanidin biosynthetic pathways in soybean and *Impatiens balsamina*, and provide genetic tools for the manipulation of these pathways.

SUMMARY OF THE INVENTION

The instant invention relates to isolated nucleic acid fragments encoding flavanone-3-hydroxylase from soybean and *Impatiens balsamina*. Specifically, this invention concerns an isolated nucleic acid fragment encoding a flavanone-3-hydroxylase. In addition, this invention relates to a nucleic acid fragment that is complementary to the nucleic acid fragment encoding flavanone-3-hydroxylase.

An additional embodiment of the instant invention pertains to a polypeptide encoding all or a substantial portion of a flavanone-3-hydroxylase.

In another embodiment, the instant invention relates to a chimeric gene encoding a flavanone-3-hydroxylase, or to a chimeric gene that comprises a nucleic acid fragment that is complementary to a nucleic acid fragment encoding a flavanone-3-hydroxylase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a flavanone-3-hydroxylase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a flavanone-3-hydroxylase in a transformed host cell comprising: a) transforming a host cell with a chimeric gene comprising a nucleic acid fragment encoding a flavanone-3-hydroxylase; and b) growing the transformed host cell under conditions that are suitable for expression of the chimeric gene wherein expression of the chimeric gene results in production of altered levels of flavanone-3-hydroxylase in the transformed host cell.

An addition embodiment of the instant invention concerns a method for obtaining a nucleic acid fragment encoding all or a substantial portion of an amino acid sequence encoding a flavanone-3-hydroxylase.

A further embodiment of the instant invention is a method for evaluating at least one compound for its ability to inhibit the activity of a flavanone-3-hydroxylase, the method comprising the steps of: (a) transforming a host cell with a chimeric gene comprising a nucleic acid fragment encoding a flavanone-3-hydroxylase, operably linked to suitable regulatory sequences; (b) growing the transformed host cell under conditions that are suitable for expression of the chimeric gene wherein expression of the chimeric gene results in production of flavanone-3-hydroxylase in the transformed host cell; (c) optionally purifying the flavanone-3-hydroxylase expressed by the transformed host cell; (d) treating the flavanone-3-hydroxylase with a compound to be tested; and (e) comparing the activity of the flavanone-3-hydroxylase that has been treated with a test compound to the activity of an untreated flavanone-3-hydroxylase, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 depicts the amino acid sequence alignment between the flavanone-3-hydroxylase from soybean clone sfl1.pk0040.g11 (SEQ ID NO:2) amino acids 7 through 375 and *Matthiola incana* (NCBI gi Accession No. 729506, SEQ ID NO:3) amino acids 3 through 357. Amino acids which are identical among both sequences are displayed in the center line while conservative substitutions are indicated with a plus sign (+). Dashes are used by the program to maximize the alignment of the sequences. The probably metal bindig residues (His-77, His-219, Asp-221 and His-277, in the soybean sequence) are boxed in black and written in white.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone sfl1.pk0040.g11 encoding an entire soybean flavanone-3-hydroxylase.

SEQ ID NO:2 is the deduced amino acid sequence of an entire soybean flavanone-3-hydroxylase derived from the nucleotide sequence of SEQ ID NO:1.

SEQ ID NO:3 is the amino acid sequence of a *Matthiola incana* flavanone-3-hydroxylase, NCBI General Identifier No. 729505.

SEQ ID NO:4 is the nucleotide sequence comprising a portion of the cDNA insert in clone ids.pk0013.g5 encoding the N-terminal sequence of a garden balsam flavonol-3-hydroxylase.

SEQ ID NO:5 is the deduced amino acid sequence of the N-terminal sequence of a garden balsam flavonol-3-hydroxylase derived from the nucleotide sequence of SEQ ID NO:4.

SEQ ID NO:6 is the nucleotide sequence comprising a portion of the cDNA insert in clone ids.pk0013.g5 encoding the C-terminal third of a garden balsam flavonol-3-hydroxylase.

SEQ ID NO:7 is the deduced amino acid sequence of the C-terminal third of a garden balsam flavonol-3-hydroxylase derived from the nucleotide sequence of SEQ ID NO:6.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under stringent conditions (0.1×SSC, 0.1% SDS, 65° C.), with the sequences exemplified herein. Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are greater than 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Percent identity was calculated using the BLASTP algorithm available from the National Center for Biotechnology Information. Default parameters were used (gap penalty=11, gap extension=1).

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the flavonol-3-hydroxylase proteins as set forth in SEQ ID NOs:2, 5 and 7. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) Nature (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of two flavanone-3-hydroxylases have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

| Flavonoid Biosynthetic Enzyme | | |
|---|---|---|
| Enzyme | Clone | Plant |
| flavanone-3-hydroxylase | sfl1.pk0040.g11 | Soybean |
| | ids.pk0013.g5 | Garden Balsam |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other flavanone-3-hydroxylases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed flavanone-3-hydroxylases are present at higher or lower levels than normal or in cell types or developmental stages in which they are not normally found. This would have the effect of altering the level of flavonols, anthocynidins, catechins and proanthocyanidins in those cells. Manipulation of the expression level of any one of these products in a plant will influence the color, disease resistance and types of oil present.

Overexpression of the flavanone-3-hydroxylase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant flavanone-3-hydroxylase to different cellular compartments, or to facilitate its secretion from the cell. It is thus envisioned that the chimeric gene described above may be further supplemented by altering the coding sequence to encode flavanone-3-hydroxylase with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding flavanone-3-hydroxylase in plants for some applications. In order to accomplish this, a chimeric gene designed for co-suppression of the instant flavanone-3-hydroxylase can be constructed by linking a gene or gene fragment encoding a flavanone-3-hydroxylase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant flavanone-3-hydroxylases (or portions thereof) may be produced in heterologous host cells, particularly in the cells of microbial hosts, and can be used to prepare antibodies to the these proteins by methods well known to those skilled in the art. The antibodies are useful for detecting flavanone-3-hydroxylases in situ in cells or in vitro in cell extracts. Preferred heterologous host cells for production of the instant flavanone-3-hydroxylases are microbial hosts. Microbial expression systems and expression vectors containing regulatory sequences that direct high level expression of foreign proteins are well known to those skilled in the art. Any of these could be used to construct a chimeric gene for production of the instant flavanone-3-hydroxylase. This chimeric gene could then be introduced into appropriate microorganisms via transformation to provide high level expression of the encoded flavanone-3-hydroxylase. An example of a vector for high level expression of the instant flavanone-3-hydroxylase in a bacterial host is provided (Example 5).

Additionally, the instant flavanone-3-hydroxylase can be used as a target to facilitate design and/or identification of inhibitors of those enzymes that may be useful as herbicides. This is desirable because the flavanone-3-hydroxylase described herein catalyzes the 3-beta-hydroxylation of 2S-flavonones to 2R, 3R-dihydroflavonones. Accordingly, inhibition of the activity of the enzyme described herein could lead to inhibition plant growth. Thus, the instant flavanone-3-hydroxylase could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bematzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the flavanone-3-hydroxylase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a flavanone-3-hydroxylase can be identified and obtained. This mutant plant can then be used to determine or confirm the natural function of the flavanone-3-hydroxylase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from soybean and garden balsam tissues were prepared. The characteristics of the libraries are described below.

TABLE 2 cDNA Libraries from Soybean and Garden Balsam

| Library | Tissue | Clone |
|---|---|---|
| sfl1 | Soybean Immature Flower | sfl1.pk0040.g11 |
| ids | *Impatiens balsamia* Developing Seed | ids.pk0013.g5 | cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding flavanone-3-hydroxylase were identified by conducting BLAST (Basic Local Alignment Search Tool; Altschul, S. F., et al., (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Flavanone-3-Hydroxylase

The BLASTX search using the EST sequences from clones s2.21h08, sre.pk0035.b1 and sfl1.pk0004.e7 revealed similarity of the proteins encoded by the cDNAs to flavanone-3-hydroxylase from *Matthiola incana* (SWISS-PROT Accession No. Q05965). The BLASTX search using the EST sequence from clone sfl1.pk0040.g11 revealed similarity of the protein encoded by the cDNAs to flavanone-3-hydroxylase from *Medicago sativa* (GenBank Accession No. X81812). The BLASTX search using the EST sequence from clone ids.pk0013.q5 revealed similarity of the protein encoded by the cDNA to flavanone-3-hydroxylase from Malus sp. (SWISS-PROT Accession No. Q06942). The BLAST results for each of these ESTs are shown in Table 3:

TABLE 3

BLAST Results for Clones Encoding Polypeptides Homologous to Flavanone-3-Hydroxylase

| Clone | Database | Accession No. | Organism | pLog |
|---|---|---|---|---|
| s2.21h08 | SWISS-PROT | Q05965 | *Matthiola incana* | 71.30 |
| sre.pk0035.b1 | SWISS-PROT | Q05965 | *Matthiola incana* | 52.11 |
| sfl1.pk0004.e7 | SWISS-PROT | Q05965 | *Matthiola incana* | 77.80 |
| sfl1.pk0040.g11 | GenBank | X81812 | *Medicago sativa* | 47.29 |
| ids.pk0013.q5 | SWISS-PROT | Q06942 | Malus sp. | 26.00 |

The sequence of the entire cDNA insert in clone sfl1.pk0040.g11 was determined and is shown in SEQ ID NO:1; this sequence includes the partial sequences from clones s2.21h08, sre.pk0035.b1 and sfl1.pk0004.e7. The deduced amino acid sequence of this cDNA is shown in SEQ ID NO:2. The amino acid sequence set forth in SEQ ID NO:2 was evaluated by BLASTP, yielding a pLog value of 176 versus the *Matthiola incana* sequence. FIG. 1 presents the BLASTP alignment of the amino acid sequence set forth in SEQ ID NO:2 and the *Matthiola incana* sequence. The BLASTP analysis shows that the soybean flavanone-3-hydroxylase sequence is 80% identical to the *Matthiola incana* sequence. The sequence of a portion of the cDNA insert from clone ids.pk0013.q5 is shown in SEQ ID NO:4; the deduced amino acid sequence of this cDNA is shown in SEQ ID NO:5. Comparison to the Malus sp. sequence indicates that this clone represents the 5' end of the gene encoding the amino terminus. The 3' terminus of this clone has also been sequenced. The BLASTX search using the EST sequences from the 3' termninus of clone ids.pk0013.q5 revealed similarity of the protein encoded by the cDNA to flavanone-3-hydroxylase from *Arabidopsis thaliana* (NCBI General Identifier No. 3790548) with a pLog value of 70.3. The sequence of the 3' terminal portion of the cDNA insert from clone ids.pk0013.q5 is shown in SEQ ID NO:6; the deduced amino acid sequence of this cDNA is shown in SEQ ID NO:7.

Sequence alignments and BLAST scores and probabilities indicate that the instant nucleic acid fragments encode an entire soybean flavanone-3-hydroxylase and portions of the N-terminus and the C-terminus of garden balsam flavanone-3-hydroxylase. These sequences represent the first soybean and garden balsam sequences encoding flavanone-3-hydroxylase.

Example 4

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant flavanol-3-hydroxylase in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding flavanol-3-hydroxylase. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the flavanol-3-hydroxylase and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 5

Expression of Chimeric Genes in Microbial Cells

The cDNAs encoding the instant flavanol-3-hydroxylase can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the flavanol-3-hydroxylase are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 6

Evaluating Compounds for Their Ability to Inhibit the Activity of Flavanol-3-Hydroxylase The flavanol-3-hydroxylases described herein may be produced using any number of methods known to those skilled in the art. Such methods include, but are not limited to, expression in bacteria as described in Example 5, or expression in eukaryotic cell culture, in planta, and using viral expression systems in suitably infected organisms or cell lines. The instant flavanol-3-hydroxylase may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-termninal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant flavanol-3-hydroxylase, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the flavanol-3-hydroxylase are expressed as fusion proteins, the purification protocol may include the use of an affinity resin which is specific for the fusion protein tag attached to the expressed enzyme or an affinity resin containing ligands which are specific for the enzyme. For example, a flavanol-3-hydroxylase may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the flavanol-3-hydroxylases disclosed herein. Assays may be conducted under well known experimental conditions which permit optimal enzymatic activity. For example, assays for flavanol-3-hydroxylase are presented by Lukacin, R. and Britsch, L. (1997) *Eur J Biochem* 249:748–757.

What is claimed is:

1. An isolated polynucleotide comprising:
   (a) a nucleotide sequence encoding a polypeptide having flavanone-3-hydroxylase activity, wherein the amino acid sequence of the polypeptide and the amino acid sequence of SEQ ID NO:2 have at least 85% sequence identity based on BLASTP algorithm, or
   (b) the complement of the nucleotide sequence, wherein the complement and the nucleotide sequence contain the same number of nucleotides and are 100% complementary.

2. The polynucleotide sequence of claim 1, wherein the amino acid sequence of the polypeptide and the amino acid sequence of SEQ ID NO:2 have at least 90% sequence identity.

3. The polynucleotide sequence of claim 1, wherein the amino acid sequence of the polypeptide and the amino acid sequence of SEQ ID NO:2 have at least 95% sequence identity.

4. The polynucleotide of claim 1, wherein the polypeptide comprises the amino acid sequence of SEQ ID NO:2.

5. The polynucleotide of claim 1, wherein the nucleotide sequence comprises the nucleotide sequence of SEQ ID NO:1.

6. A cell comprising the polynucleotide of claim 1.

7. A transgenic plant comprising the polynucleotide of claim 1.

8. A method for transforming a cell comprising introducing into a cell the polynucleotide of claim 1.

9. A method for producing a transgenic plant comprising (a) transforming a plant cell with the polynucleotide of claim 1, and (b) regenerating a transgenic plant from the transformed plant cell.

10. A vector comprising the polynucleotide of claim 1.

11. A recombinant DNA construct comprising the polynucleotide of claim 1 operably linked to a regulatory sequence.

12. A cell comprising the recombinant DNA construct of claim 11.

13. A plant comprising the recombinant DNA construct of claim 11.

14. A seed comprising the recombinant DNA construct of claim 11.

* * * * *

UNITED STATES PATENT AND TRADEMARK OFFICE
CERTIFICATE OF CORRECTION

PATENT NO.     : 6,570,064 B1
DATED          : May 27, 2003
INVENTOR(S)    : Allen Stephen M., Fader Gary M. and Kinney Anthony J.

It is certified that error appears in the above-identified patent and that said Letters Patent is hereby corrected as shown below:

<u>Title page,</u>
Item [60], Related U.S. Application Data, please change as follows: -- Continuation of application No. PCT/US99/03200 filed on Feb. 16, 1999. Provisional application No. 60/075,919, filed on Feb 25, 1998. --

Signed and Sealed this

Third Day of August, 2004

JON W. DUDAS
*Acting Director of the United States Patent and Trademark Office*

```
                        SEQUENCE LISTING

<160> NUMBER OF SEQ ID NOS:  7

<210> SEQ ID NO 1
<211> LENGTH: 1465
<212> TYPE: DNA
<213> ORGANISM: Glycine max

<400> SEQUENCE: 1
gcacgagggc acgaggaagc attgcattct gctatttaat tccactacgt acacgcacat      60
tctcctcaaa gacaacaatg gcaccaacag ccaagactct gacttacctg gcccaggaga     120
aaaccctaga atcgagcttc gttcgggacg aggaggagcg tcccaaggtt gcctacaacg     180
aattcagcga cgagatccca gtgatttctc ttgccggaat cgacgaggtg gatggacgca     240
gaagagagat ttgtgagaag atcgtggagg cttgcgagaa ttggggtata ttccaggttg     300
ttgatcacgg tgtggatcaa caactcgtgg ccgagatgac ccgtctcgcc aaagagttct     360
ttgctttgcc accggacgag aagcttcgtt ttgatatgtc cggcgccaaa aagggtggat     420
tcattgtctc cagccatctc caaggggaat cggtgcagga ctggagagaa atagtgacat     480
actttctgta cccaaaaaga gagagggact attcaaggtg gccagacacg ccagaagggt     540
ggagatcggt gactgaggaa tacagcgaca aagtaatggg tctagcttgc aagctcatgg     600
aggtgttgtc cgaagcaatg gggttagaga aagagggttt aagcaaagca tgtgttgaca     660
tggaccagaa ggtggtggtt aattactacc ccaaatgccc tcaacctgac ctcactcttg     720
gcctgaagcg ccacacggat ccgggcacta tcaccttgct gcttcaggac caagtgggtg     780
gacttcaagc caccagggac aatggcaaaa catggatcac cgttcagcct gtggaggctg     840
ccttcgtcgt caatcttgga gatcatgctc attatctgag caatgaaagg ttcaagaatg     900
ctgatcacca agcggtggtg aactcaaacc atagccgttt gtccatagcc actttttcaaa    960 acccagcacc aaatgcaact gtttaccctc tgaagataag agaaggagag aagcctgtga    1020
tggaggaacc aatcactttt gctgaaatgt acaggaggaa gatgagcaag gacattgaga    1080
ttgcaaggat gaagaagctg gctaaggaaa agcatttgca ggaccttgag aatgaaaagc    1140
atttgcaaga acttgatcag aaggcaaaac ttgaggccaa gcctttgaag gagattcttg    1200
cttaattaat aataattaca tatgtatcat ttgcatgccc ccttggtgtt tttagtattt    1260
```

```
tttaagggcc atgaattaat aatagtcctt acctttgtgc ttttgtacgt cttatgattt    1320
atcctttgtg gggatatcat gtgttgtgtt cagttgccta tgtcttatta gctagctggc    1380
tcatctatgt ataccttata tgtgcctcta ttataaatga aataagtgg cactgtcttt     1440 attaaaaaaa aaaaaaaaaa aaaaa                                           1465
```

<210> SEQ ID NO 2
<211> LENGTH: 375
<212> TYPE: PRT
<213> ORGANISM: Glycine max

<400> SEQUENCE: 2

```
Met Ala Pro Thr Ala Lys Thr Leu Thr Tyr Leu Ala Gln Glu Lys Thr
 1               5                  10                  15

Leu Glu Ser Ser Phe Val Arg Asp Glu Glu Arg Pro Lys Val Ala
                20                  25                  30

Tyr Asn Glu Phe Ser Asp Glu Ile Pro Val Ile Ser Leu Ala Gly Ile
                35                  40                  45

Asp Glu Val Asp Gly Arg Arg Arg Glu Ile Cys Glu Lys Ile Val Glu
    50                  55                  60

Ala Cys Glu Asn Trp Gly Ile Phe Gln Val Val Asp His Gly Val Asp
 65                  70                  75                  80

Gln Gln Leu Val Ala Glu Met Thr Arg Leu Ala Lys Glu Phe Phe Ala
                85                  90                  95

Leu Pro Pro Asp Glu Lys Leu Arg Phe Asp Met Ser Gly Ala Lys Lys
                100                 105                 110

Gly Gly Phe Ile Val Ser Ser His Leu Gln Gly Glu Ser Val Gln Asp
            115                 120                 125

Trp Arg Glu Ile Val Thr Tyr Phe Ser Tyr Pro Lys Arg Glu Arg Asp
        130                 135                 140

Tyr Ser Arg Trp Pro Asp Thr Pro Glu Gly Trp Arg Ser Val Thr Glu
145                 150                 155                 160

Glu Tyr Ser Asp Lys Val Met Gly Leu Ala Cys Lys Leu Met Glu Val
                165                 170                 175

Leu Ser Glu Ala Met Gly Leu Glu Lys Glu Gly Leu Ser Lys Ala Cys
                180                 185                 190

Val Asp Met Asp Gln Lys Val Val Asn Tyr Tyr Pro Lys Cys Pro
            195                 200                 205

Gln Pro Asp Leu Thr Leu Gly Leu Lys Arg His Thr Asp Pro Gly Thr
        210                 215                 220

Ile Thr Leu Leu Gln Asp Gln Val Gly Gly Leu Gln Ala Thr Arg
225                 230                 235                 240

Asp Asn Gly Lys Thr Trp Ile Thr Val Gln Pro Val Glu Ala Ala Phe
                245                 250                 255

Val Val Asn Leu Gly Asp His Ala His Tyr Leu Ser Asn Gly Arg Phe
                260                 265                 270

Lys Asn Ala Asp His Gln Ala Val Val Asn Ser Asn His Ser Arg Leu
            275                 280                 285

Ser Ile Ala Thr Phe Gln Asn Pro Ala Pro Asn Ala Thr Val Tyr Pro
        290                 295                 300

Leu Lys Ile Arg Glu Gly Glu Lys Pro Val Met Glu Glu Pro Ile Thr
305                 310                 315                 320

Phe Ala Glu Met Tyr Arg Arg Lys Met Ser Lys Asp Ile Glu Ile Ala
                325                 330                 335
```

```
Arg Met Lys Lys Leu Ala Lys Glu Lys His Leu Gln Asp Leu Glu Asn
            340                 345                 350

Glu Lys His Leu Gln Glu Leu Asp Gln Lys Ala Lys Leu Glu Ala Lys
            355                 360                 365

Pro Leu Lys Glu Ile Leu Ala
            370             375

<210> SEQ ID NO 3
<211> LENGTH: 357
<212> TYPE: PRT
<213> ORGANISM: Matthiola incana

<400> SEQUENCE: 3

Ala Pro Gly Thr Leu Thr Glu Leu Ala Gly Glu Ser Lys Leu Asn Ser
 1               5                  10                  15

Lys Phe Val Arg Asp Glu Asp Glu Arg Pro Lys Val Ala Tyr Asn Glu
            20                  25                  30

Phe Ser Asp Glu Ile Pro Val Ile Ser Leu Ala Gly Ile Asp Asp Val
            35                  40                  45

Asp Gly Lys Arg Gly Glu Ile Cys Arg Glu Ile Val Glu Ala Cys Glu
    50                  55                  60

Asn Trp Gly Ile Phe Gln Val Val Asp His Gly Val Asp Thr Ser Leu
65                  70                  75                  80

Val Ala Asp Met Thr Arg Leu Ala Arg Asp Phe Phe Ala Leu Pro Pro
                85                  90                  95

Glu Glu Lys Leu Arg Phe Asp Met Ser Gly Lys Lys Gly Phe
            100                 105                 110

Ile Val Ser Ser His Leu Gln Gly Glu Ala Val Gln Asp Trp Arg Glu
            115                 120                 125

Ile Val Thr Tyr Phe Ser Tyr Pro Val Arg Asn Arg Asp Tyr Ser Arg
            130                 135                 140

Trp Pro Asp Lys Pro Gln Gly Trp Ala Lys Val Thr Glu Glu Tyr Ser
145                 150                 155                 160

Glu Lys Leu Met Gly Leu Ala Cys Lys Leu Leu Glu Val Leu Ser Glu
                165                 170                 175

Ala Met Gly Leu Glu Lys Glu Ser Leu Thr Asn Ala Cys Val Asp Met
            180                 185                 190

Asp Gln Lys Ile Val Val Asn Tyr Tyr Pro Lys Cys Pro Gln Pro Asp
            195                 200                 205

Leu Thr Leu Gly Leu Lys Arg His Thr Asp Pro Gly Thr Ile Thr Leu
            210                 215                 220

Leu Leu Gln Asp Gln Val Gly Gly Leu Gln Ala Thr Arg Asp Asp Gly
225                 230                 235                 240

Asn Thr Trp Ile Thr Val Gln Pro Val Glu Gly Ala Phe Val Val Asn
                245                 250                 255

Leu Gly Asp His Gly His Phe Leu Ser Asn Gly Arg Phe Lys Asn Ala
            260                 265                 270

Asp His Gln Ala Val Val Asn Ser Asn Ser Ser Arg Leu Ser Ile Ala
            275                 280                 285

Thr Phe Gln Asn Pro Ala Pro Glu Ala Thr Val Tyr Pro Leu Lys Val
            290                 295                 300

Arg Glu Gly Glu Lys Ala Ile Met Glu Glu Pro Ile Thr Phe Ala Glu
305                 310                 315                 320

Met Tyr Lys Arg Lys Met Gly Arg Asp Leu Glu Leu Ala Arg Leu Lys
                325                 330                 335
```

Lys Leu Ala Lys Glu Glu His Asn His Lys Glu Ala Ala Lys Pro Leu
            340                 345                 350

Asp Gln Ile Leu Ala
        355

<210> SEQ ID NO 4
<211> LENGTH: 604
<212> TYPE: DNA
<213> ORGANISM: Impatiens balsamina
<220> FEATURE:
<221> NAME/KEY: unsure
<222> LOCATION: (234)..(235)
<221> NAME/KEY: unsure
<222> LOCATION: (282)
<221> NAME/KEY: unsure
<222> LOCATION: (285)
<221> NAME/KEY: unsure
<222> LOCATION: (293)
<221> NAME/KEY: unsure
<222> LOCATION: (296)
<221> NAME/KEY: unsure
<222> LOCATION: (340)
<221> NAME/KEY: unsure
<222> LOCATION: (366)
<221> NAME/KEY: unsure
<222> LOCATION: (368)
<221> NAME/KEY: unsure
<222> LOCATION: (380)
<221> NAME/KEY: unsure
<222> LOCATION: (388)
<221> NAME/KEY: unsure
<222> LOCATION: (401)
<221> NAME/KEY: unsure
<222> LOCATION: (403)
<221> NAME/KEY: unsure
<222> LOCATION: (406)
<221> NAME/KEY: unsure
<222> LOCATION: (427)
<221> NAME/KEY: unsure
<222> LOCATION: (429)
<221> NAME/KEY: unsure
<222> LOCATION: (443)
<221> NAME/KEY: unsure
<222> LOCATION: (445)
<221> NAME/KEY: unsure
<222> LOCATION: (466)
<221> NAME/KEY: unsure
<222> LOCATION: (478)
<221> NAME/KEY: unsure
<222> LOCATION: (496)
<221> NAME/KEY: unsure
<222> LOCATION: (505)
<221> NAME/KEY: unsure
<222> LOCATION: (525)
<221> NAME/KEY: unsure
<222> LOCATION: (531)
<221> NAME/KEY: unsure
<222> LOCATION: (538)
<221> NAME/KEY: unsure
<222> LOCATION: (540)
<221> NAME/KEY: unsure
<222> LOCATION: (542)
<221> NAME/KEY: unsure
<222> LOCATION: (553)
<221> NAME/KEY: unsure
<222> LOCATION: (558)..(559)
<221> NAME/KEY: unsure
<222> LOCATION: (568)
<221> NAME/KEY: unsure
<222> LOCATION: (581)
<221> NAME/KEY: unsure
<222> LOCATION: (589)

<400> SEQUENCE: 4
gagctctttc tctctccctc tctcacgtac gttctggaga atcaaccagt tatgtcgcct        60

-continued

```
gtggagacac taacctcgat cgcggaggag aagacgcttc gacagaagtt tgtcagggac    120
gaagacgagc ggcctaaggt tgcctacaat gtattcagca ccgttgtacc ggttatctcg    180
ctcgccggaa tcgacgaagt ggaaggacgg agagccgaga tctgtaagaa acgnnttgat    240
gctttgtgaa gattggggaa ttttcaagtc cgtgggtcac gnggnttgat tcnaaccta     300 accccgggat aatgatccgc tcgtccgcga gtcttcggcn atgccgccgg aggaagaatc    360
ccattngnat gcccgggggn aagaaggngt ttaattgccc nancancttc aggaaaacct    420
tcaagtngng tgaatgtact atncncgacc tcccggaacc ggatanccaa atggcggnaa    480
gcaaacgtgg atcctnaagg gactnatgga attagggttg gccgnaatgc ngaatgtntn    540
gngcaaggaa tgnaaaannt gctaagangt aaatgtaaaa ngggattna ccaatgccca     600 cttt                                                                 604
```

<210> SEQ ID NO 5
<211> LENGTH: 73
<212> TYPE: PRT
<213> ORGANISM: Impatiens balsamina
<220> FEATURE:
<221> NAME/KEY: UNSURE
<222> LOCATION: (62)
<221> NAME/KEY: UNSURE
<222> LOCATION: (66)

<400> SEQUENCE: 5

```
Met Ser Pro Val Glu Thr Leu Thr Ser Ile Ala Glu Glu Lys Thr Leu
  1               5                  10                  15

Arg Gln Lys Phe Val Arg Asp Glu Asp Glu Arg Pro Lys Val Ala Tyr
             20                  25                  30

Asn Val Phe Ser Thr Val Val Pro Val Ile Ser Leu Ala Gly Ile Asp
         35                  40                  45

Glu Val Glu Gly Arg Arg Ala Glu Ile Cys Lys Lys Arg Xaa Asp Ala
     50                  55                  60

Leu Xaa Arg Leu Gly Asn Phe Gln Val
 65                  70
```

<210> SEQ ID NO 6
<211> LENGTH: 144
<212> TYPE: PRT
<213> ORGANISM: Impatiens balsamina

<400> SEQUENCE: 6

```
Thr Leu Leu Leu Gln Asp Gln Val Gly Gly Leu Gln Ala Thr Arg Asp
  1               5                  10                  15

Gly Gly Lys Thr Trp Ile Thr Val Gln Pro Val Glu Gly Ala Phe Val
             20                  25                  30

Val Asn Leu Gly Asp His Gly His Phe Leu Ser Asn Gly Arg Phe Arg
         35                  40                  45

Asn Ala Asp His Gln Ala Val Val Asn Ser Asn His Ser Arg Leu Ser
     50                  55                  60

Ile Ala Thr Phe Gln Asn Pro Ala Pro Asp Ala Ile Val Tyr Pro Leu
 65                  70                  75                  80

Lys Val Arg Asp Gly Glu Lys Ala Val Met Glu Glu Ala Ile Thr Phe
                 85                  90                  95

Ala Glu Met Tyr Lys Arg Lys Met Ser Lys Asp Leu Glu Leu Ala Lys
                100                 105                 110

Leu Lys Lys Leu Ala Lys Glu Lys Leu Glu Glu Glu Leu Glu Lys
            115                 120                 125
```

-continued

```
Ala Lys Leu Asn Ile Val Lys Ala Lys Asp Ala Gly Glu Ile Phe Ala
    130                 135                 140

<210> SEQ ID NO 7
<211> LENGTH: 506
<212> TYPE: DNA
<213> ORGANISM: Impatiens balsamina

<400> SEQUENCE: 7
ccatactctt cttcttcaag atcaggtcgg cggtcttcaa gcaactaggg acggtggtaa      60
gacctggatc actgttcaac ctgttgaggg agccttcgtc gttaacttag gcgaccatgg     120
ccattttctg agcaacggca ggttcaggaa tgcagaccat caagcggtgg tgaactcaaa     180
ccatagccgc ctgtcaatcg cgacgtttca gaacccggct ccagatgcga ttgtttatcc     240
attgaaggtt agggatggag agaaggcagt gatggaggaa gcgataactt ttgcagagat     300
gtacaagagg aagatgagta aggacctgga actggccaag ttgaagaaac tggccaagga     360
gaaactggaa gaagaagagc tggaaaaggc caagctaaat attgttaagg ccaaagacgc     420
tggagagatc tttgcttaga attaattatg tttgtttttt atattaagta ttgctactttt    480 ttttcttaaa aaaaaaaaaa aaaaaa                                          506
```